United States Patent [19]

Moore et al.

[11] Patent Number: 5,532,346
[45] Date of Patent: Jul. 2, 1996

[54] HYDROXYNAPHTHALENECARBOXYLIC ACID COMPOUNDS AND AZO COLORANTS MADE THEREFROM

[75] Inventors: Patrick D. Moore, Pacolet; Michael A. Valenti, Taylors; Richard A. VanDahm, Spartanburg, all of S.C.

[73] Assignee: Milliken Research Corporation, Spartanburg, S.C.

[21] Appl. No.: 327,375

[22] Filed: Oct. 21, 1994

[51] Int. Cl.$^6$ .......................... C09B 29/20; C09B 67/22
[52] U.S. Cl. .......................... 534/729; 534/864; 564/180; 106/23 K; 106/494
[58] Field of Search .......................... 534/729, 864; 564/180

[56] References Cited

U.S. PATENT DOCUMENTS

| | | | |
|---|---|---|---|
| 1,987,669 | 1/1935 | Dahlen | 260/124 |
| 2,328,734 | 9/1943 | Marriott et al. | 260/560 |
| 3,034,892 | 5/1962 | Gledhill et al. | 96/55 |
| 3,207,748 | 9/1965 | Bossard et al. | 260/204 |
| 3,299,013 | 1/1967 | Umberger | 260/78.5 |
| 3,507,850 | 4/1970 | Cohen et al. | 534/729 X |
| 3,644,518 | 2/1972 | Yoshida et al. | 260/559 |
| 4,113,721 | 9/1978 | Hauser et al. | 534/729 |
| 4,187,246 | 2/1980 | Spivak et al. | 260/559 |
| 4,317,682 | 3/1982 | Katsura et al. | 106/288 |
| 4,468,255 | 8/1984 | Schwartz et al. | 106/288 |
| 4,871,371 | 10/1989 | Harris | 534/729 X |
| 5,062,894 | 11/1991 | Schwartz et al. | 106/23 |
| 5,176,745 | 1/1993 | Moore et al. | 106/22 |
| 5,286,287 | 2/1994 | Hirasawa et al. | 106/22 |
| 5,290,921 | 3/1994 | Moody et al. | 534/607 |
| 5,312,926 | 5/1994 | Bach et al. | 548/195 |

FOREIGN PATENT DOCUMENTS

| | | | |
|---|---|---|---|
| 63-264674 | 4/1987 | Japan | 534/729 |
| 2036779 | 7/1980 | United Kingdom | 534/729 |

*Primary Examiner*—Floyd D. Higel
*Attorney, Agent, or Firm*—Tim Monahan; Terry T. Moyer

[57] ABSTRACT

A coupling component for use in the synthesis of azo colorants, selected from compounds having the formula:

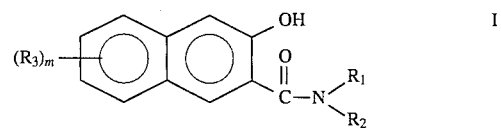

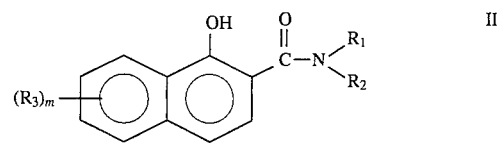

wherein $R_1$ is Y or arylene-$(Y)_n$, where n is an integer from 1–4; $R_2$ is H, $C_1$–$C_8$ alkyl, $C_3$–$C_8$ cycloalkyl, aryl, or Y; provided that if $R_1$ is arylene-$(Y)_n$, then $R_2$ is not aryl; $R_3$ is $C_1$–$C_4$ alkyl, $C_1$–$C_4$ alkoxy, $SO_3H$, Br, Cl, OH, or $NO_2$ and m is an integer from 0–3; and Y is a poly(oxyalkylene) substituent having from 4–200 oxyalkylene units which are the addition products of compounds selected from the group consisting of ethylene oxide and propylene oxide.

14 Claims, 1 Drawing Sheet

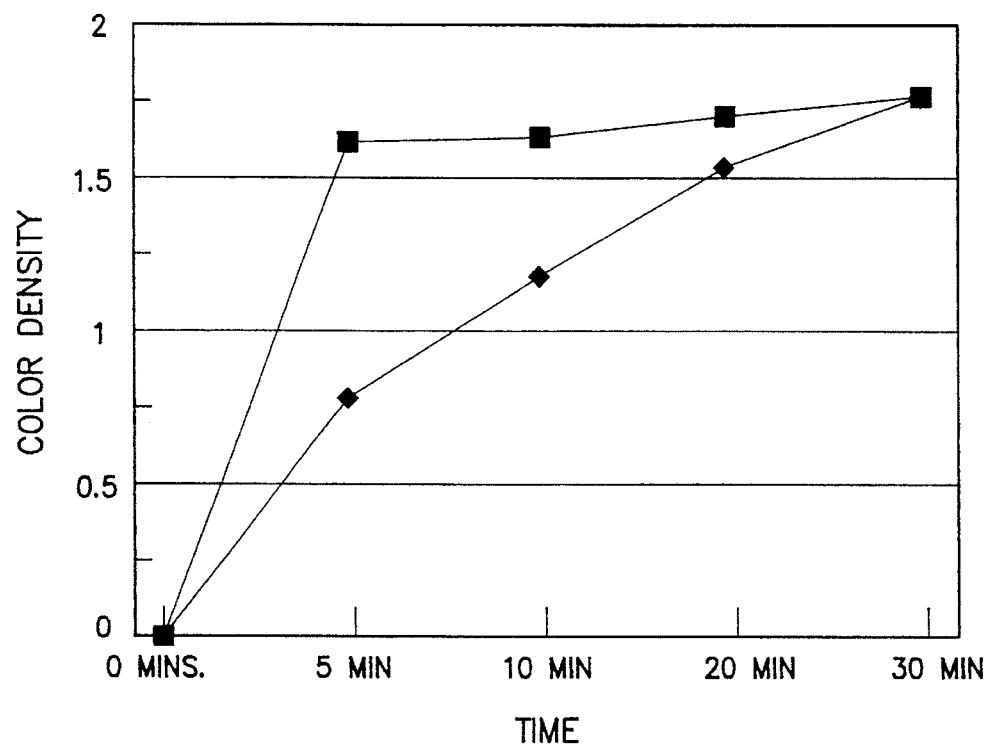
FIG. —1—
■ PIGMENT CONTAINING POLY(OXYALKLENE) SUBSTITUTED COUPLER
♦ COMMERCIAL PIGMENT

HYDROXYNAPHTHALENECARBOXYLIC ACID COMPOUNDS AND AZO COLORANTS MADE THEREFROM

BACKGROUND OF THE INVENTION

The present invention relates to derivatives of 1-hydroxy-2-naphthalenecarboxylic acid (1-hydroxy-2-naphthoic acid) and BON acid (3-hydroxy-2-naphthalenecarboxcylic acid; 3-hydroxy-2-naphthoic acid; or β-oxynaphthoic acid) having a poly(oxyalkylene) substituent, and in particular to poly(oxyalkylene) substituted amide derivatives of such acids. The scope of the invention also includes azo colorants which incorporate the hydroxynaphthalenecarboxylic acid derivatives as a coupling component.

The use of hydroxynaphthalenecarboxylic acid as a coupling component in azo colorants is well known. For example, Lithol Rubine (Pigment Red 57), Permanent Red 2B (Pigment Red 48), Yellow BON Maroon (Pigment Red 55), and Lithol Red 2G (Pigment Red 52) are all synthesized by coupling the diazonium salt of a primary aromatic amine to BON acid.

Arylamides of BON acid have also been employed as azo coupling components, such as Naphthol AS. Azoic or naphthol pigment dyes made from these arylamides have been found to have greater substantivity for cotton than those made with the corresponding BON acid component. Examples of arylamides of BON acid may be found in Marriott, et al., U.S. Pat. No. 2,328,734 and Glendill et al., U.S. Pat. No. 3,034,892. Amides of BON acid and either benzylamine or phenylethylamine are disclosed in Hirasawa et al. U.S. Pat. No. 5,286,287. The coupling components are useful in manufacturing monoazo pigments for printing inks.

Disazo colorants may be made from amide derivatives of BON acid. Two moles of BON acid are first convened to the acid chloride, followed by condensation with an aromatic diamine. Dahlen, U.S. Pat. No. 1,987,669 discloses a BON acid and aromatic diamine condensation product which is useful as a dye intermediate for disazo colorants. The aromatic diamines may be linked by a diethylether group.

Further examples of amide derivatives of hydroxynapthalenecarboxylic acid which have an ether constituent may be found in the following patents: Bossard, et al., U.S. Pat. No. 3,207,748—intermediates for hydrophobic azo dyestuffs; Umberger, et al., U.S. Pat. No. 3,299,013—vinyl containing dye intermediates for use in color photography; and Yoshida et al., U.S. Pat. No. 3,644,518—process for producing 1-hydroxy-2-naphthamide derivatives. The aforementioned dye intermediates illustrate up to two oxyalkylene groups in the amide substituent.

Colorants and colorant intermediates having poly(oxyalkylene) substituents are disclosed in the following patent publications: Toyo, Ink., Japanese Kokai Patent No. 63[1989]-264674—pigment having improved dispersability; Schwartz, et al., U.S. Pat. No. 4,468,255 and Schwartz, et al., U.S. Pat. No. 5,062,894—poly(oxyalkylene) modified arylide and diarylide pigments; Moore, et al., U.S. Pat. No. 5,176,745—aqueous ink compositions; and Moody, et al., U.S. Pat. No. 5,290,921—intermediates and colorants having branched poly(oxyalkylene) substituents. These colorants have found applications in areas of inks, fugitive tints for textiles, thermoplastic resins and thermosetting resins.

Although a large number of poly(oxyalkylene) substituted colorants appear in the prior art, a poly(oxyalkylene) substituted derivative of hydroxynaphthalenecarboxylic acid or azo colorant made therefrom has not been disclosed. In the typical synthesis of amide derivatives of hydroxynaphthalenecarboxylic acid, the dye intermediate is recovered by crystallization and filtration. However, the enhanced solubility and liquidity of typical poly(oxyalkylene) substituted intermediates and colorants have deterred adoption of such prior art techniques. Thus, despite the extensive use of hydroxynaphthalenecarboxylic acid and amide derivatives of hydroxynaphthalenecarboxylic acid in the manufacture of colorants, a poly(oxyalkylene) substituted derivative of hydroxynaphthalenecarboxylic acid or an azo colorant made therefrom, has not been heretofore available. All of the aforementioned patents are incorporated herein by reference.

BRIEF DESCRIPTION OF THE DRAWINGS

FIG. 1 is a graph of color density versus time during which a pigment of the present invention and a commercial (prior art) pigment are milled.

SUMMARY OF THE INVENTION

Therefore, an object of the invention is to provide a poly(oxyalkylene) substituted derivative of hydroxynaphthalenecarboxylic acid, which may be used as a coupling component in the manufacture of azo colorants.

Another object of the invention is to provide a poly(oxyalkylene) substituted amide derivative of hydroxynaphthalenecarboxylic acid by a route that substantially reduces undesired byproducts.

Accordingly, an amide derivative of a 1-hydroxy-2-naphthalenecarboxylic acid or 3-hydroxy-2-naphthalenecarboxylic acid intermediate is provided, wherein the amido group of the intermediate has at least one poly(oxyalkylene) substituent characterized as having from 4 to 200 oxyalkylene units, which are the addition products of $C_2$-$C_4$ alkylene oxides. The naphthyl component of the intermediate may be substituted, as is known in the art, for example with from 0 to 3 groups selected from the group consisting of $C_1$-$C_4$ alkoxy, $SO_3H$, Br, Cl, OH and $NO_2$. The amido component of the intermediate may be derived from an aryl amine.

Also within the scope of the present invention is an azo colorant made by coupling the diazonium salt of an aromatic primary amine to the intermediate. In an alternative invention, a mixture of the poly(oxyalkylene) substituted hydroxynaphthalenecarboxylic acid and hydroxynaphthalenecarboxylic acid are coupled to the diazonium salt to produce a pigment having improved properties.

The subject invention have been found to have the following advantages and features: ♦ the poly(oxyalkylene) substituent may be constructed to provide liquidity, solubility and dispersability in a wide range of aqueous and organic solvents; ♦ azo colorants which have decreased particle density strength and require less milling; and ♦ a poly(oxyalkylene) substituted derivative of hydroxynaphthalenecarboxylic acid which is substantially free from impurities.

DETAILED DESCRIPTION OF THE INVENTION

Without limiting the scope of the invention, the preferred embodiments and features are herein after set forth. Unless otherwise indicated, all parts and percentages are by weight, and conditions are ambient, i.e. one atmosphere of pressure and 25 C. The terms aryl and arylene are intended to be limited to single and fused double ring aromatic hydrocarbons. Unless otherwise specified, aliphatic hydrocarbons are from 1–12 carbons in length, and cycloaliphatic hydrocarbons compromise from 3–8 carbons.

The novel colorant intermediates of the present invention can be characterized by one or the other of the following structures, depending on whether the hydroxy group is in the "1" or "3" position respectively:

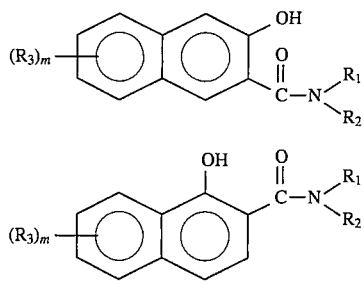

wherein $R_1$ is Y or arylene-$(Y)_n$, where n is an integer from 1–4; preferably $R_1$ is Y or phenylene-$(Y)_n$ and n=1 or 2;

$R_2$ is H, $C_1$–$C_8$ alkyl, aryl, or Y; provided that if $R_1$ is arylene-$(Y)_n$, then $R_2$ is not aryl; preferably $R_2$ is H;

$R_3$ is $C_1$–$C_4$ alkyl, $C_1$–$C_4$ alkoxy, $SO_3H$, Br, Cl, OH, or $NO_2$ and m is an integer from 0–3; preferably $R_3$ is $CH_3$, $OCH_3$, $SO_3H$, Br, or OH and m is 0, 1 or 2, most preferably m is 0.

Y is a poly(oxyalkylene) substituent having from 4 to 200 oxyalkylene units which are primarily the addition products of ethylene oxide or propylene oxide or random and block copolymers thereof. Minor amounts of the addition products of glycidol and butylene oxide and other compatible monomers may be present without deviating from the scope of the invention. Preferably, Y has from 6 to 20 oxyalkylene units.

The precise identity of the terminal group of Y is not deemed to be critical to the invention. Suitable terminal groups include alkyl ethers, especially methyl ether, phenyl ether, alkyl, and phenyl esters, and carboxy-terminated alkyl and alkenyl esters. Additionally, by way of example, and not limitation, the following terminal groups may be employed: —$OCH_2C(O)OH$, —SH, —OH, —$NH_2$, —$OC(O)NH_2$, —OP(O)(k)j, —$OC(O)R_4$ and sulfonate and sulfates of each of the members of said group wherein are $R_4$ is an alkyl or alkenyl radical containing up to 20 carbon atoms or a carboxy-terminated alkyl or alkenyl radical containing up to 20 carbon atoms, j and k are OH, OM, or $OR_5$ wherein M is a cation moiety of an alkali metal, alkaline earth metal, transition metal, e.g. nickel, etc., or ammonium, and $R_5$ is an alkyl radical containing up to 20 carbon atoms.

Also within the scope of the present invention, is the reaction product of an amine terminated poly(oxyalkylene) substituted hydroxynaphthalenecarboxylic acid derivative and a second hydroxynaphthalenecarboxylic acid to form a dimer linked together by the poly(oxyalkylene) substituent. Suitable poly(oxyalkylene) diamines are available from Texaco Chemical Company, Tex., U.S.A. under the Jeffamine™ product line.

In cases where $R_1$ is arylene-Y, the poly(oxyalkylene) substituent may be bonded to the arylene group by, for example, an oxy, amino, sulfonamido, thio, or carboxy group, as is known in the art. Preferably, the poly(oxyalkylene) substituent is bonded to the arylene group by O, N($R_4$), N, $SO_2N(R_4)$, $SO_2N$, where $R_4$ is $C_1$–$C_8$ alkyl or phenyl.

The arylene or aryl radicals designated in $R_1$ and $R_2$ respectively, may contain one or more substituent groups as is known in the art, such as $C_1$–$C_4$ alkoxy, $C_1$–$C_4$ alkyl, Br, Cl, and $NO_2$.

Synthesis

The intermediates of the present invention may be synthesized by the following procedure. A slurry of hydroxynaphthalenecarboxylic acid in toluene is converted to the acid chloride by the reaction with thionyl chloride in a presence of a catalytic amount of dimethylformamide (DMF). Next, sodium bicarbonate is added followed by a poly(oxyalkylene) substituted amine. The sodium bicarbonate neutralizes the acid released by formation of the amide and avoids formation of byproducts, such as the ammonium salts of the poly(oxyalkylene) amine, which would otherwise be very difficult and costly to separate from the amide derivative of hydroxynaphthalenecarboxylic acid given there similarity and solubility.

Examples 1–4 demonstrates formation of the poly(oxyalkylene) substituted amide derivative of BON acid.

EXAMPLE ONE

One half mole (94.0 g) of 3-hydroxy-2-naphthoic acid (BON Acid) is slurried into 500 mL of anhydrous toluene and purged with nitrogen. Thirteen hundredths of a mole (10 mL) moles of dimethylformamide is added to the slurry and the mixture is heated to 40 C. for 10 minutes. Next, 0.52 (61.0 g) moles of thionyl chloride is added slowly to the mixture with a slight exotherm and the reaction mixture is heated to 60 C. for 2 hrs, to form the acid chloride. The formation of sulfur dioxide and HCl during the reaction is removed with a trap containing 50% NaOH. While maintaining the temperature at 60 C., vacuum is applied for one hour to remove any remaining sulfur dioxide. The batch is cooled to 45 C. and 45 g of sodium bicarbonate is added in 5 gram increments followed by 0.67 (220 g) moles of an amine adduct that contains 5 moles of propylene oxide. The reaction is heated to 75 C. for 2 hrs, then cooled to 65 C. and washed with 400 g of water. The organic layer is separated and toluene is vacuum stripped, leaving the polymeric amide (256 g) with the following average structure:

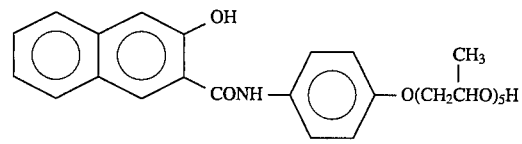

EXAMPLE TWO

The acid chloride step is prepared as in Example One. The batch is cooled to 45 C. and 45 g of sodium bicarbonate is added in 5 gram increments followed by 0.52 moles (370 grams) of Jeffamine M 715™ (Texaco). The reaction is heated to 75 C. for 2 hrs, then cooled and washed with 400 g of water. The organic layer is separated and toluene is vacuum stripped leaving the polymeric amide (380 g) with the following average structure:

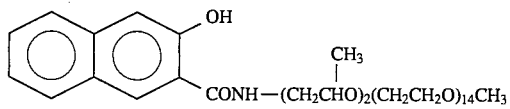

EXAMPLE THREE

The acid chloride step is prepared as in Example One. The batch is cooled to 45 C. and 45 g of sodium bicarbonate is added in 5 gram increments, followed by 0.67 moles (670 grams) of an amine adduct containing 13 moles of propylene oxide. The reaction is heated to 75 C. for 2 hrs, then cooled to 65 C. and washed with 400 g of water. The organic layer is separated and toluene vacuum stripped leaving the polymeric amide with the following average structure:

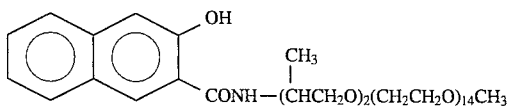

EXAMPLE FOUR

Two hundred sixty six thousandths of a mole (50.0 g) of 3-hydroxy-2-naphthoic acid is mixed with 229 g of an amine adduct that contains 13 moles of propylene oxide. The mixture is heated to 240 C. under a nitrogen blanket, and a dean-stark trap. The evolution of water occurs and mixture becomes homogenous. The reaction was monitored by GPC and showed formation of a polymeric amide, 84% completion after 12 hrs, with the following average structure:

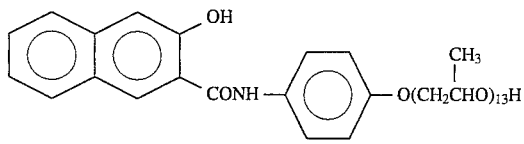

The poly(oxyalkylene) substituted amide derivative of hydroxynaphthalenecarboxylic acid has utility as an intermediate in the manufacture of azo colorants. Azo colorants are traditionally manufactured by (1) diazotization of a primary aromatic amine followed by (2) coupling the resulting diazonium salt with the hydroxynaphthalenecarboxylic acid. The reaction is well documented in the literature, such as in Venkataraman, *The Chemistry of Synthetic Dyes*, Vo. I, Chapters IV and XI (1952).

A vast number of diazotizable primary aromatic amines are known in the art of dye manufacturing. For example, diazonium salts may be formed from primary amines based on phenyl, naphthyl, or five and six membered heterocyclic compounds containing from 1–3 hetero atoms selected from S, N, and O which optionally may be benzo-fused. By way of further example, primary amines based upon the following heterocyclic, aromatic structures may be employed: thiazolyl, benzothiazolyl, thiadiazolyl, isothiazolyl, isoxazolyl, benzisothiazolyl, thienyl, pyridyl, pyrazolyl, triazolyl, and phthalimidyl. Preferably, the diazotized primary aromatic amine used to couple with the hydroxynaphthalenecarboxylic acid derivative is a phenyl or naphthyl amine, for example, 2-amino-5-methyl-benzene sulfonic acid and 2-chloro-4-amino toluene-5-sulfonic acid.

As is well known in the art, the diazo component may be substituted with, by way of example and not limitation, one or more groups selected from alkyl, preferably, methyl, sulfonic, chloro, bromo, carboxyl, nitro, alkoxy, preferably methoxy, cyano, trifluoromethyl, alkylthio, arylthio, and hydroxy.

The coupling reaction between the diazonium salt of the aromatic amine and the hydroxynaphthalenecarboxylic acid derivative may be accomplished using standard techniques as shown in the following example.

EXAMPLE FIVE

Twenty five parts of the polymeric amide from Example Two is added to 75 parts water and the mixture is neutralized to pH of 12.0 with 50% NaOH. To a separate flask, 80 parts of an ethoxylated aminophenol is mixed with 25 parts water and 23 parts of HCl. This mixture is cooled to 0–5 C. Approximately 15 g of sodium nitrite is slowly added, and the resulting diazo mixture is allowed to stir for approximately 1 hour. Excess diazo is neutralized with sulfamic acid and the diazo is then coupled with the polymeric amide solution. The resulting red solution is allowed to stir for 2 hrs. and then neutralized to 6.5–7.5 with ammonium hydroxide. The solution is heated to 70 C. and transferred to a separatory funnel. The salt layer is drained and the product layer is stripped, leaving a dark liquid colorant with a lamda max at approximately 500 nm. The colorant has the following average structure:

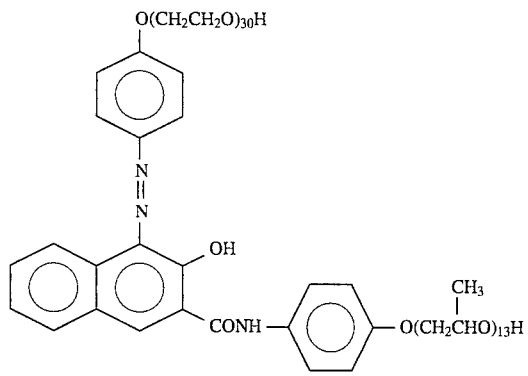

In another embodiment of the invention, the poly(oxyalkylene) amide derived hydroxynaphthalenecarboxylic acid (polymeric hydroxynaphthalenecarboxylic acid) is blended with a "standard coupler", such as 1-hydroxy-2-naphthalenecarboxylic acid, BON acid, BON acid amide derivative which does not contain the poly(oxyalkylene) substituent such as amides of BON acid and a compound selected from aniline, benzylamine, phenylethylamine and five membered heterocyclic aromatics as disclosed in U.S. Pat. No. 5,312,926, incorporated by reference, or 13- naphthol, in a ratio of from 1:99 to 99:1, preferably 5:95 to 70:30 of the polymeric hydroxynaphthalenecarboxylic acid and the standard coupler, respectfully. The mixture of polymeric hydroxynaphthalenecarboxylic acid and standard coupler is then coupled to the appropriate diazo component to form an azo pigment containing a portion of poly(oxyalkylene) substituted azo compounds. It is believed that the presence of the poly(oxyalkylene) substituent in the pigment particle, enhances dispersability and allows for the pigment to be more easily milled, as the particles appear to be more friable. The friability of the azo colorant particles made with a blend of hydroxynaphthalenecarboxylic acid and poly(oxyalkylene) substituted amide derivatives is surprising considering that the azo colorant made with 100% of the poly(oxyalkylene) substituted amide derivatives is liquid. As will be apparent to those skilled in the art, the standard coupler is intended to include hydroxynaphthalenecarboxylic acids which are substituted with, for example, up to three groups selected from $C_1$–$C_4$ alkyl, $C_1$–$C_4$ alkoxy, $SO_3H$, Br, Cl, OH and $NO_2$.

The synthesis of an azo colorant from the mixture of BON acid and the poly(oxyalkylene) substituted amide derivatives of BON acid (50:50) is shown in the following example.

EXAMPLE SIX

Part 1

One half mole of the adduct from Example 3 is mixed with 0.5 moles of 3-hydroxy-2-naphthoic acid, water, and 50% sodium hydroxide to a pH of approximately 11.0.

Part 2

In a separate flask, 37.4 g of 2-amino-5-methyl benzene sulfonic acid (4B acid) is mixed with 200 g of water and heated to 60 C. for 10 minutes. The mixture is cooled to room temperature and 4.4 g of 50% sodium hydroxide is added and allowed to mix. Fourteen and two tenths grams of sodium nitrite is dissolved in 30 mL of water and added to the reaction mixture. The mixture is then cooled to 5 C. Then, 61.1 g of 37% HCl is added dropwise, keeping the temperature of the mixture at less than 10 C. This diazo mixture is allowed to stir for 1.5 hours. The mixture from Part 1 is added to Part 2, keeping the temperature at approximately 30 C., and allowed to stir for approximately 1 hour. Forty three and six tenths grams of barium chloride is dissolved 24 g of water, added to the reaction, and allowed to stir for 10 minutes. The reaction is heated to 60 C. for 1 hour. The final product is a solid and is filtered, washed and dried to give a yield of 79.5%. The product, is highly disperable in toluene and is insoluble in methanol and water. The final product is expected to be a hybrid or mixture of the following average structures:

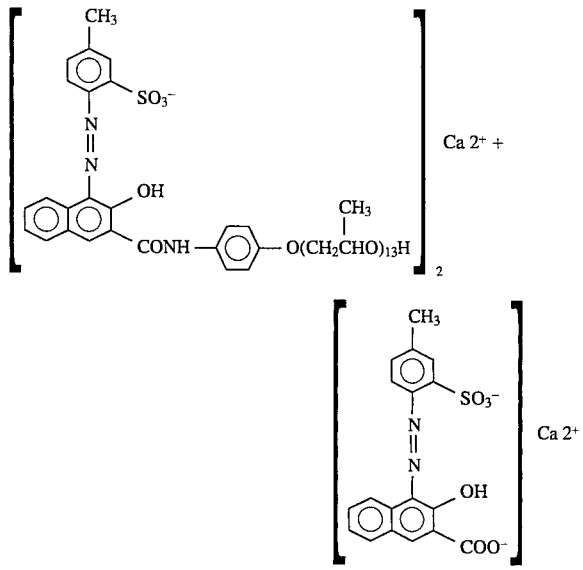

The enhanced dispersability of the azo colorant made from a 50:50 mixture of hydroxynaphthalenecarboxylic acid and the hydroxynaphthalenecarboxylic acid derivative of the present invention is demonstrated by the following comparison with the corresponding azo pigment made with 100% hydroxynaphthalenecarboxylic acid intermediate (commercial pigment).

EXAMPLE SIX

Comparative Example

The product from Example Five was dispersed in a resin base and toluene in the ratio of 53.0 resin(50% solids)/26.1 product/20.9 toluene, using the quick mill method, which consists of a steel can filled with steel shot placed on a paint shaker. This material showed superior dispersability over shorter time periods when compared to standard pigment controls prepared with all conventional materials.

Referring to FIG. 1, the dispersability of the colorant of Example 6 and a standard pigment, as measured by density, is plotted over a 30 minute time period. The differences are dramatic: the azo colorant made from the 50:50 mixture of BON acid and the poly(oxyalkylene) substituted amide derivative of BON acid was over 90% dispersed in 5 minutes compare to 44% dispersion for the standard pigment in the same time period.

The colorant of the present invention includes azo colorants synthesized from the poly(oxyalkylene) substituted amide derivative of hydroxynaphthalenecarboxylic acid coupling component, as well as colorants synthesized from a mixture of the poly(oxyalkylene) substituted amide derivative of hydroxynaphthalenecarboxylic acid and up to 99 mole percent of a standard coupler, preferably those selected from 1-hydroxy-2-naphthalenecarboxylic acid, BON acid, BON acid amides without a poly(oxyalkylene) substituent, such as Naphthol AS, and 13 naphthol.

The aforementioned colorants are particularly useful in printing ink formulations. By way of example, colorants may be used in gravure inks and offset inks. A typical gravure ink composition contains from:

(i) 2–25 parts colorant;

(ii) 5–35 parts resin;

(iii) 50–93 parts solvent; and (iv) up to 15 parts miscellaneous additives.

The colorant component may be a pigment, dye and includes extenders such as opacifiers and clays. The colorant of the present invention may constitute all or pan of the colorant component of the gravure ink formulation.

By way of example and not limitation, the resin may be selected from the following compounds: rosin and modified rosins, such as calcium, magnesium and zinc metallic resinates, ester gum or rosin, maleic resins and esters, dimerized and polymerized rosins and rosin modified fumaric resins; shellac, asphalts phenolic resins and rosin-modified phenolic resins; alkyd resins; polystyrene resins and copolymers thereof; terpene resins; alkylated urea formaldehyde resins; alkylated melamine formaldehyde resins; polyamide resins; polyamide resins; vinyl resins, such as polyvinyl acetate and polyvinyl alcohol; ketone resins; acrylic resins, such as polyacrylic acid and polymethacrylic acid; epoxide resins; polyurethane resins; cellulosic resins, such as nitro cellulose, ethyl cellulose, cellulose acetate butyrate and carboxymethyl cellulose.

By way of further example, the solvents may be selected from toluene, xylene, $C_5$–$C_{40}$ aliphatic and cycloaliphatic hydrocarbons, 1,1 1-trichloroethane, and methylene chloride. Miscellaneous additives include plasticizers, waxes, surfactants, defoaming agents, catalysts, antioxidants, corrosion inhibitors, biocides and deodorants.

The formulation of printing inks is well known and is described in detail in *The Printing Ink Manual*, 4th Edition, edited by Dr. R. H. Leach, et al. (1988).

There are of course, many alternate embodiments and modifications of the invention, which are intended to be included within the scope of the following claims.

What we claim is:

1. A coupling component selected from the group consisting of compounds having the formula:

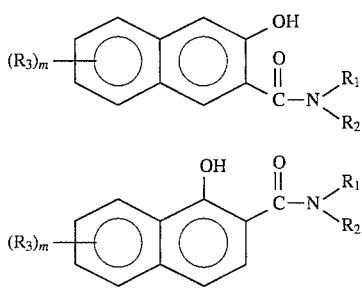

wherein $R_1$ is Y or arylene-$(Y)_n$, where n is an integer from 1–4; $R_2$ is H, $C_1$–$C_8$ alkyl, $C_3$–$C_8$ cycloalkyl, aryl, or Y; provided that if $R_1$ is arylene-$(Y)_n$, then $R_2$ is not aryl; $R_3$ is $C_1$–$C_4$ alkyl, $C_1$–$C_4$ alkoxy, $SO_3H$, Br, Cl, OH, or $NO_2$ and m is an integer from 0–3; and Y is a poly(oxyalkylene) substituent having from 4–200 oxyalkylene units which are the addition products of compounds selected from the group consisting of ethylene oxide and propylene oxide.

2. The coupling component of claim 1, wherein $R_1$ is Y or phenylene-$(Y)_n$ and n is 1 or 2; $R_2$ is H; and $R_3$ is $CH_3$, $OCH_3$, $SO_3H$, Br, or OH and m is 0, 1 or 2.

3. The coupling component of claim 1, wherein $R_1$ is Y or phenylene-$(Y)_n$ and n is 1 or 2; $R_2$ is H; and $R_3$ is $CH_3$, $OCH_3$, $SO_3H$, Br, or OH, m is 0 or 1 and Y has from 6 to 20 oxyalkylene units.

4. The coupling component of claim 1 wherein said coupling component has the structure of formula I and $R_1$ is Y, $R_2$ is H and m is 0.

5. An azo colorant which is the product of coupling a diazotized aromatic amine with a coupling component selected from the group consisting of compounds of the formula:

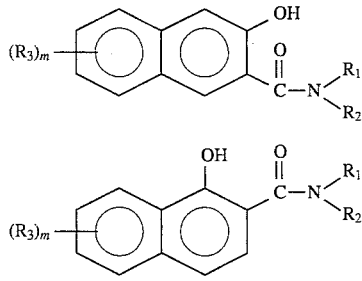

wherein $R_1$ is Y or arylene-$Y)_n$, where n is an integer from 1–4; $R_2$ is H, $C_1$–$C_8$ alkyl, $C_3$–$C_8$ cycloalkyl, aryl, or Y; provided that if $R_1$ is arylene-$(Y)_n$, then $R_2$ is not aryl; $R_3$ is $C_1$–$C_4$ alkyl, $C_1$–$C_4$ alkoxy, $SO_3H$, Br, Cl, OH, or $NO_2$ and m is an integer from 0–3; and Y is a poly-(oxyalkylene) substituent having from 4–2000 oxyalkylene units which are the addition products of compounds selected from the group consisting of ethylene oxide and propylene oxide.

6. The azo colorant of claim 5 wherein said diazotized aromatic amine is the diazonium salt of a primary amine comprising a radical selected from the group consisting of phenyl, naphthyl, and five and six membered heterocyclic compounds and benzo-fused heterocyclic compounds containing from one to three hetero atoms selected from the group consisting of S, N, and O, said radical is unsubstituted or substituted with one or more groups selected from alkyl, sulfonic, chloro, bromo, carboxyl, nitro, alkoxy, cyano, trifluoromethyl, alkylthio, arylthio and hydroxy, and wherein $R_1$ is Y or phenylene-$(Y)_n$ and n is 1 or 2; $R_2$ is H; and $R_3$ is $OCH_3$, $SO_3H$, Br, or OH and m is 0, 1 or 2.

7. The azo colorant of claim 5 wherein said radical is selected from the group consisting of phenyl, naphthyl, thiazolyl, benzothiazolyl, thiadiazolyl, isothiazolyl, isoxazolyl, benzisothiazolyl, thienyl, pyridyl, pyrazolyl, triazolyl, and phthalimidyl; wherein $R_1$ is Y or phenylene-$(Y)_n$ and n is 1 or 2; $R_2$ is H; and $R_3$ is $CH_3$, $OCH_3$, $SO_3H$, Br, or OH and m is 0, 1 or 2; and Y has from 6 to 20 oxyalkylene units.

8. The azo colorant of claim 6 wherein said coupling component has the structure of formula I and $R_1$ is Y, $R_2$ is H and m is 0.

9. The azo colorant of claim 8 wherein said diazotized aromatic amine is the diazonium salt of a primary amine selected from the group consisting of 2-amino-5-methylbenzene sulfonic acid and 2-chloro-4 amino-toluene-5-sulfonic acid.

10. An azo pigment comprising a plurality of azo colorants which are the product of coupling a plurality of diazotized aromatic amines with a plurality of coupling components, wherein from 1:99 parts by weight of said coupling components are selected from the group consisting of components of the formula:

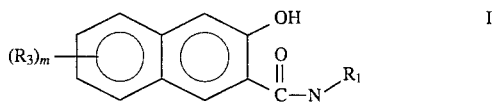

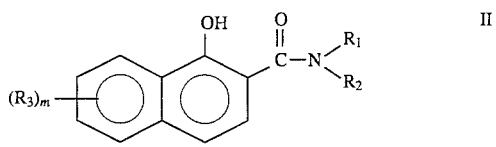

wherein $R_1$ is Y or arylene-$(Y)_n$, where n is an integer from 1–4; $R_2$ is H, $C_1$–$C_8$ alkyl, $C_3$–$C_8$ cycloalkyl aryl, or Y; provided that if $R_1$ is arylene-$(Y)_n$, then $R_2$ is not aryl; $R_3$ is $C_1$–$C_4$ alkyl, $C_1$–$C_4$ alkoxy, $SO_3H$, Br, Cl, OH, or $NO_2$ and m is an integer from 0–3; and Y is a poly(oxyalkylene) substituent having from 4–200 oxyalkylene units which are the addition products of compounds selected from the group consisting of ethylene oxide and propylene oxide; and from 99:1 parts of said coupling components are selected from the group consisting of 1-hydroxy-2 naphthalenecarboxylic acid, BON acid, β-naphthol, and amides of BON acid and a compound selected from the group consisting of aniline, benzylamine, and phenylethylamine.

11. The azo pigment of claim 10 wherein each of said diazotized aromatic amines is the diazonium salt of a primary amine comprising a radical selected from a group consisting of phenyl, naphthyl, and five and six membered heterocyclic compounds and benzo-fused heterocyclic compounds containing from one to three hetero atoms selected from the group consisting of S, N and O, said radical is unsubstituted or substituted with one or more groups selected from alkyl, sulfonic, chloro, bromo, carboxyl, nitro, alkoxy, cyano, trifluoromethyl, alkylthio, arylthio and hydroxy, and wherein $R_1$ is Y or phenylene-$(Y)_n$ and n is 1 or 2; $R_2$ is H; and $R_3$ is $CH_3$, $OCH_3$, $SO_3H$, Br, or OH and m is 0, 1 or 2.

12. The azo pigment of claim 10 wherein said radical is selected from the group consisting of phenyl, naphthyl, thiazolyl, benzothiazolyl, thiadiazolyl, isothiazolyl, isoxazolyl, benzisothiazolyl, thienyl, phyridyl, pyrazolyl, triazolyl, and phthalimidyl; wherein $R_1$ is Y or phenylene-$(Y)_n$ and n is 1 or 2; $R_2$ is H; and $R_3$ is $CH_3$, $OCH_3$, $SO_3H$, Br, or OH and m is 0, 1 or 2; and Y has from 6 to 20 oxyalkylene units.

13. The azo pigment of claim 11 wherein from 5 to 70 parts by weight of said coupling components have the structure of formula I and $R_1$ is Y, $R_2$ is H and m is 0.

14. The azo pigment of claim 13 wherein each of said diazotized aromatic amines is the diazonium salt of a primary amine selected from the group consisting of 2-amino-5-methylbenzene sulfonic acid and 2-chloro-4 amino-toluene-5-sulfonic acid.

* * * * *